US009358010B2

(12) United States Patent
Wenchell et al.

(10) Patent No.: US 9,358,010 B2
(45) Date of Patent: Jun. 7, 2016

(54) FLEX CABLE AND SPRING-LOADED TUBE FOR TACKING DEVICE

(71) Applicant: Covidien LP, Mansfield, MA (US)

(72) Inventors: Thomas Wenchell, Durham, CT (US); Roberto Pedros, Oxford, CT (US); Johana Molina, New Haven, CT (US)

(73) Assignee: Covidien LP, Mansfield, MA (US)

( * ) Notice: Subject to any disclaimer, the term of this patent is extended or adjusted under 35 U.S.C. 154(b) by 70 days.

(21) Appl. No.: 14/199,096

(22) Filed: Mar. 6, 2014

(65) Prior Publication Data

US 2014/0276969 A1 Sep. 18, 2014

Related U.S. Application Data

(60) Provisional application No. 61/776,811, filed on Mar. 12, 2013.

(51) Int. Cl.
*A61B 17/10* (2006.01)
*A61B 17/068* (2006.01)
*A61B 17/064* (2006.01)
*A61B 17/29* (2006.01)

(52) U.S. Cl.
CPC ............ *A61B 17/10* (2013.01); *A61B 17/068* (2013.01); *A61B 2017/0648* (2013.01); *A61B 2017/2905* (2013.01); *A61B 2017/2923* (2013.01)

(58) Field of Classification Search
CPC ...... A61B 17/10; A61B 17/08; A61B 17/068; A61B 2017/0648; A61B 2017/2905; A61B 2017/2923
USPC .................................. 606/139–143
See application file for complete search history.

(56) References Cited

U.S. PATENT DOCUMENTS

| 3,866,510 | A | 2/1975 | Eibes |
| 4,884,572 | A | 12/1989 | Bays |
| 5,085,661 | A | 2/1992 | Moss |

(Continued)

FOREIGN PATENT DOCUMENTS

| DE | 10300787 A1 | 9/2004 |
| DE | 10 2010 015009 | 10/2011 |

(Continued)

OTHER PUBLICATIONS

Extended European Search Report corresponding to EP 14 15 8946. 5, completed Jun. 20, 2014 and mailed Jul. 8, 2014; (9 pp).

(Continued)

*Primary Examiner* — Katrina Stransky

(57) ABSTRACT

A surgical fastener applier is disclosed and includes a handle portion, a tubular member extending from the handle portion and defining a longitudinal axis, a drive member rotatably supported in the tubular member and in the handle portion, and a plurality of fasteners. The drive member is configured to rotate while in a deflected condition with respect to the longitudinal axis. The drive member includes a proximal portion, a central portion, and a distal portion, the central portion being relatively more flexible configuration as compared to at least one of the proximal portion and the distal portion. The plurality of fasteners is disposed within the tubular member and is configured to engage a portion of the drive member such that rotational motion of the drive member causes distal advancement of at least one fastener of the plurality of fasteners through the tubular member.

10 Claims, 11 Drawing Sheets

(56) References Cited

U.S. PATENT DOCUMENTS

| | | | |
|---|---|---|---|
| 5,171,247 A | 12/1992 | Hughett |
| 5,171,249 A | 12/1992 | Stefanchik |
| 5,176,306 A | 1/1993 | Heimerl |
| 5,207,697 A | 5/1993 | Carusillo |
| 5,228,256 A | 7/1993 | Dreveny |
| 5,236,563 A | 8/1993 | Loh |
| 5,246,441 A | 9/1993 | Ross |
| 5,246,450 A | 9/1993 | Thornton |
| 5,312,023 A | 5/1994 | Green |
| 5,330,487 A | 7/1994 | Thornton |
| 5,344,061 A | 9/1994 | Crainich |
| 5,356,064 A | 10/1994 | Green |
| 5,382,254 A | 1/1995 | McGarry |
| 5,398,861 A | 3/1995 | Green |
| 5,403,327 A | 4/1995 | Thornton |
| 5,433,721 A | 7/1995 | Hooven |
| 5,439,468 A | 8/1995 | Schulze |
| 5,466,243 A | 11/1995 | Schmieding |
| 5,467,911 A | 11/1995 | Tsuruta |
| 5,474,566 A | 12/1995 | Alesi |
| 5,474,567 A | 12/1995 | Stefanchik |
| 5,522,844 A | 6/1996 | Johnson |
| 5,527,319 A | 6/1996 | Green |
| 5,553,765 A | 9/1996 | Knodel |
| 5,562,685 A | 10/1996 | Mollenauer |
| 5,564,615 A | 10/1996 | Bishop |
| 5,582,615 A | 12/1996 | Foshee |
| 5,582,616 A | 12/1996 | Bolduc |
| 5,584,425 A | 12/1996 | Savage |
| 5,588,581 A | 12/1996 | Conlon |
| 5,601,571 A | 2/1997 | Moss |
| 5,601,573 A | 2/1997 | Fogelberg |
| 5,626,613 A | 5/1997 | Schmieding |
| 5,628,752 A | 5/1997 | Asnis |
| 5,649,931 A | 7/1997 | Bryant |
| 5,662,662 A | 9/1997 | Bishop |
| 5,681,330 A | 10/1997 | Hughett |
| 5,683,401 A | 11/1997 | Schmieding |
| 5,685,474 A | 11/1997 | Seeber |
| 5,697,935 A | 12/1997 | Moran |
| 5,709,692 A | 1/1998 | Mollenauer |
| 5,728,116 A | 3/1998 | Rosenman |
| 5,730,744 A | 3/1998 | Justin |
| 5,732,806 A | 3/1998 | Foshee |
| 5,735,854 A | 4/1998 | Caron |
| 5,741,268 A | 4/1998 | Schutz |
| 5,762,255 A | 6/1998 | Chrisman |
| 5,782,844 A | 7/1998 | Yoon |
| 5,810,882 A | 9/1998 | Bolduc |
| 5,824,008 A | 10/1998 | Bolduc |
| 5,830,221 A | 11/1998 | Stein |
| 5,843,087 A | 12/1998 | Jensen |
| 5,897,564 A | 4/1999 | Schulze |
| 5,904,693 A | 5/1999 | Dicesare |
| 5,910,105 A | 6/1999 | Swain |
| 5,911,722 A | 6/1999 | Adler |
| 5,928,244 A | 7/1999 | Tovey |
| 5,928,252 A | 7/1999 | Steadman |
| 5,931,844 A | 8/1999 | Thompson |
| 5,941,439 A | 8/1999 | Kammerer |
| 5,954,259 A | 9/1999 | Viola |
| 5,961,524 A | 10/1999 | Crombie |
| 5,964,772 A | 10/1999 | Bolduc |
| 5,976,160 A | 11/1999 | Crainich |
| 5,997,552 A | 12/1999 | Person |
| 6,010,513 A | 1/2000 | Tormala |
| 6,013,991 A | 1/2000 | Philipp |
| 6,039,753 A | 3/2000 | Meislin |
| 6,074,395 A | 6/2000 | Trot |
| 6,099,537 A | 8/2000 | Sugai |
| 6,126,670 A | 10/2000 | Walker |
| 6,132,435 A | 10/2000 | Young |
| 6,146,387 A | 11/2000 | Trot |
| 6,183,479 B1 | 2/2001 | Tormala |
| 6,228,098 B1 | 5/2001 | Kayan |
| 6,235,058 B1 | 5/2001 | Huene |
| 6,241,736 B1 | 6/2001 | Sater |
| 6,261,302 B1 | 7/2001 | Voegele |
| 6,296,656 B1 | 10/2001 | Bolduc |
| 6,330,964 B1 | 12/2001 | Kayan |
| 6,387,113 B1 | 5/2002 | Hawkins |
| 6,402,757 B1 | 6/2002 | Moore, III |
| 6,425,900 B1 | 7/2002 | Knodel |
| 6,439,446 B1 | 8/2002 | Perry |
| 6,440,136 B1 | 8/2002 | Gambale |
| 6,450,391 B1 | 9/2002 | Kayan |
| 6,457,625 B1 | 10/2002 | Tormala |
| 6,551,333 B2 | 4/2003 | Kuhns |
| 6,562,051 B1 | 5/2003 | Bolduc |
| 6,572,626 B1 | 6/2003 | Knodel |
| 6,589,249 B2 | 7/2003 | Sater |
| 6,626,916 B1 | 9/2003 | Yeung |
| 6,632,228 B2 | 10/2003 | Fortier |
| 6,652,538 B2 | 11/2003 | Kayan |
| 6,663,656 B2 | 12/2003 | Schmieding |
| 6,666,854 B1 | 12/2003 | Lange |
| 6,695,867 B2 | 2/2004 | Ginn |
| 6,733,506 B1 | 5/2004 | McDevitt |
| 6,743,240 B2 | 6/2004 | Smith |
| 6,749,621 B2 | 6/2004 | Pantages |
| 6,755,836 B1 | 6/2004 | Lewis |
| 6,773,438 B1 | 8/2004 | Knodel |
| 6,824,548 B2 | 11/2004 | Smith |
| 6,837,893 B2 | 1/2005 | Miller |
| 6,840,943 B2 | 1/2005 | Kennefick |
| 6,843,794 B2 | 1/2005 | Sixto |
| 6,869,435 B2 | 3/2005 | Blake, III |
| 6,884,248 B2 | 4/2005 | Bolduc |
| 6,887,244 B1 | 5/2005 | Walker |
| 6,893,446 B2 | 5/2005 | Sater |
| 6,905,057 B2 | 6/2005 | Swayze |
| 6,929,661 B2 | 8/2005 | Bolduc et al. |
| 6,942,674 B2 | 9/2005 | Belef |
| 6,945,979 B2 | 9/2005 | Kortenbach |
| 6,960,217 B2 | 11/2005 | Bolduc |
| 6,966,919 B2 | 11/2005 | Sixto, Jr. |
| 6,988,650 B2 | 1/2006 | Schwemberger |
| 7,000,819 B2 | 2/2006 | Swayze |
| 7,128,754 B2 | 10/2006 | Bolduc |
| 7,204,847 B1 | 4/2007 | Gambale |
| 7,261,716 B2 | 8/2007 | Strobel |
| 7,670,362 B2 | 3/2010 | Zergiebel |
| 7,758,612 B2 | 7/2010 | Ship |
| 7,862,573 B2 | 1/2011 | Darois |
| 7,867,252 B2 | 1/2011 | Criscuolo |
| 7,931,660 B2 | 4/2011 | Aranyi |
| 8,002,811 B2 | 8/2011 | Corradi |
| 8,034,076 B2 | 10/2011 | Criscuolo |
| 8,075,570 B2 | 12/2011 | Bolduc et al. |
| 8,087,142 B2 | 1/2012 | Levin |
| 8,114,099 B2 | 2/2012 | Ship |
| 8,114,101 B2 | 2/2012 | Criscuolo |
| 8,216,272 B2 | 7/2012 | Ship |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi |
| 8,343,176 B2 | 1/2013 | Criscuolo |
| 8,343,184 B2 | 1/2013 | Blier |
| 8,382,778 B2 | 2/2013 | Criscuolo |
| 8,414,627 B2 | 4/2013 | Corradi |
| 8,465,520 B2 | 6/2013 | Blier |
| 8,474,679 B2 | 7/2013 | Felix |
| 8,579,919 B2 | 11/2013 | Bolduc |
| 8,579,920 B2 | 11/2013 | Nering |
| 8,597,311 B2 | 12/2013 | Criscuolo et al. |
| 8,728,120 B2 | 5/2014 | Blier |
| 8,777,969 B2 | 7/2014 | Kayan |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 2003/0009441 A1 | 1/2003 | Holsten |
| 2003/0114839 A1 | 6/2003 | Looper et al. |

(56) References Cited

U.S. PATENT DOCUMENTS

| | | |
|---|---|---|
| 2004/0092937 A1 | 5/2004 | Criscuolo |
| 2004/0111089 A1 | 6/2004 | Stevens et al. |
| 2004/0127916 A1 | 7/2004 | Bolduc et al. |
| 2004/0181222 A1 | 9/2004 | Culbert et al. |
| 2004/0204723 A1 | 10/2004 | Kayan |
| 2004/0243139 A1 | 12/2004 | Lewis et al. |
| 2006/0129152 A1 | 6/2006 | Ship |
| 2007/0038220 A1 | 2/2007 | Ship |
| 2007/0162030 A1 | 7/2007 | Aranyi |
| 2008/0086154 A1* | 4/2008 | Taylor ............. A61B 17/068 606/142 |
| 2008/0097523 A1 | 4/2008 | Bolduc |
| 2008/0147113 A1 | 6/2008 | Nobis |
| 2008/0188868 A1 | 8/2008 | Weitzner et al. |
| 2008/0243106 A1 | 10/2008 | Coe et al. |
| 2008/0281336 A1* | 11/2008 | Zergiebel ......... A61B 17/068 606/142 |
| 2008/0312687 A1 | 12/2008 | Blier |
| 2009/0118776 A1 | 5/2009 | Kelsch |
| 2009/0188965 A1 | 7/2009 | Levin |
| 2010/0030262 A1 | 2/2010 | McLean et al. |
| 2010/0270354 A1 | 10/2010 | Rimer |
| 2010/0292710 A1 | 11/2010 | Daniel |
| 2010/0292713 A1 | 11/2010 | Cohn |
| 2010/0292715 A1 | 11/2010 | Nering |
| 2011/0022065 A1 | 1/2011 | Shipp |
| 2011/0060349 A1 | 3/2011 | Cheng et al. |
| 2011/0071578 A1 | 3/2011 | Colesanti |
| 2011/0079627 A1 | 4/2011 | Cardinale |
| 2011/0087240 A1 | 4/2011 | Shipp |
| 2011/0295282 A1 | 12/2011 | Glick |
| 2012/0059397 A1 | 3/2012 | Criscuolo et al. |
| 2012/0109157 A1 | 5/2012 | Criscuolo et al. |
| 2013/0018392 A1* | 1/2013 | Zergiebel ......... A61B 17/064 606/139 |
| 2013/0110088 A1 | 5/2013 | Wenchell |
| 2013/0131700 A1 | 5/2013 | Criscuolo |
| 2013/0197591 A1 | 8/2013 | Corradi |
| 2014/0114329 A1 | 4/2014 | Zergiebel |
| 2014/0121684 A1 | 5/2014 | Criscuolo |
| 2014/0276967 A1 | 9/2014 | Fischvogt et al. |
| 2014/0276969 A1 | 9/2014 | Wenchell et al. |
| 2014/0276972 A1 | 9/2014 | Abuzaina et al. |
| 2014/0316446 A1 | 10/2014 | Kayan |
| 2014/0371765 A1 | 12/2014 | Corradi et al. |
| 2015/0001272 A1 | 1/2015 | Sniffin et al. |
| 2015/0005748 A1 | 1/2015 | Sniffin et al. |
| 2015/0005788 A1 | 1/2015 | Sniffin et al. |
| 2015/0005789 A1 | 1/2015 | Sniffin et al. |
| 2015/0018847 A1 | 1/2015 | Criscuolo et al. |
| 2015/0032130 A1 | 1/2015 | Russo |
| 2015/0080911 A1 | 3/2015 | Reed |
| 2015/0133970 A1 | 5/2015 | Ranucci et al. |
| 2015/0133971 A1 | 5/2015 | Ranucci et al. |
| 2015/0133972 A1 | 5/2015 | Ranucci et al. |

FOREIGN PATENT DOCUMENTS

| | | |
|---|---|---|
| DE | 10 2010 015009 A1 | 10/2011 |
| EP | 0 374 088 | 6/1990 |
| EP | 0 834 280 | 4/1998 |
| EP | 1 273 272 | 1/2003 |
| EP | 1 908 409 | 4/2008 |
| EP | 1990013 A1 | 11/2008 |
| EP | 2 055 241 A2 | 5/2009 |
| EP | 1908409 B1 | 12/2010 |
| EP | 2399538 A2 | 12/2011 |
| EP | 2484294 A1 | 8/2012 |
| JP | 9149906 | 6/1997 |
| WO | 00/16701 A1 | 3/2000 |
| WO | WO 00/16701 | 3/2000 |
| WO | WO 02/34140 | 5/2002 |
| WO | WO 03/034925 | 5/2003 |
| WO | WO 03/103507 | 12/2003 |
| WO | WO 2004/112841 | 12/2004 |
| WO | 2005004727 A1 | 1/2005 |
| WO | 2012/064692 A2 | 5/2012 |
| WO | 2013/046115 A1 | 4/2013 |

OTHER PUBLICATIONS

Extended European Search Report corresponding to EP 14 17 8107.0, completed Nov. 24, 2014 and mailed Dec. 3, 2014; (5 pp).
Extended European Search Report corresponding to EP 14 17 4656.0, completed Jan. 16, 2015 and mailed Jan. 26, 2015; (7 pp).
Extended European Search Report corresponding to EP 14 18 4907.5, completed Jan. 12, 2015 and mailed Jan. 27, 2015; (9 pp).
Extended European Search Report corresponding to EP 14 15 9394.7, completed Apr. 16, 2014 and mailed Apr. 29, 2014; (8 pp).
Extended European Search Report corresponding to EP No. 10 01 2659.8, completed Dec. 21, 2010 and mailed Jan. 3, 2011; 3 pages.
Extended European Search Report corresponding to EP No. 10 01 2646.5, completed Feb. 11, 2011 and mailed Feb. 22, 2011; 3 pages.
Extended European Search Report corresponding to EP No. 11 25 0549.0, completed Sep. 9, 2013 and mailed Sep. 17, 2014; 9 pages.
Extended European Search Report corresponding to counterpart application EP 14 19 7885.8 dated Apr. 30, 2015; 9pp.
Extended European Search Report corresponding to counterpart application EP 14 18 1900.3 dated Apr. 9, 2015; 7pp.

* cited by examiner

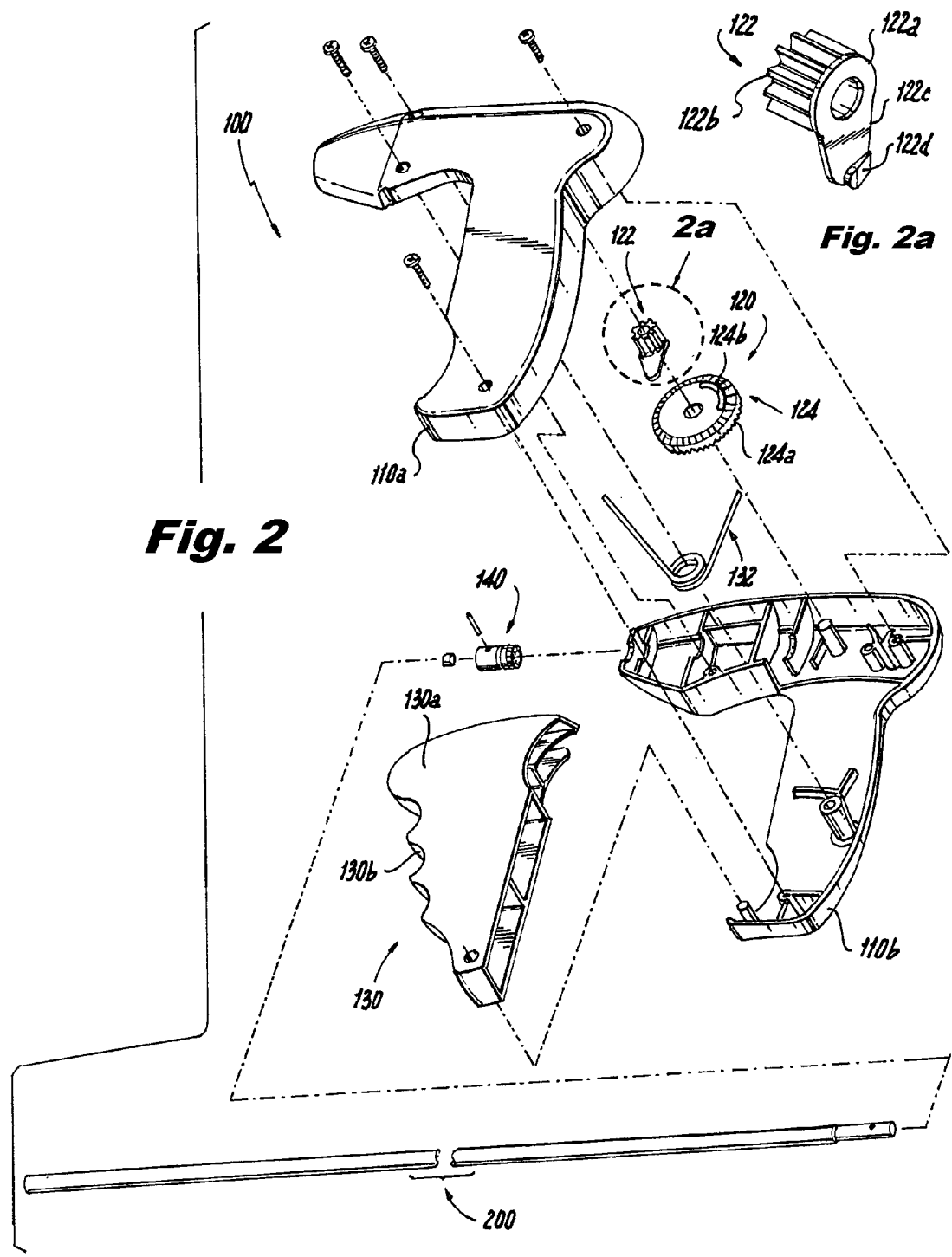

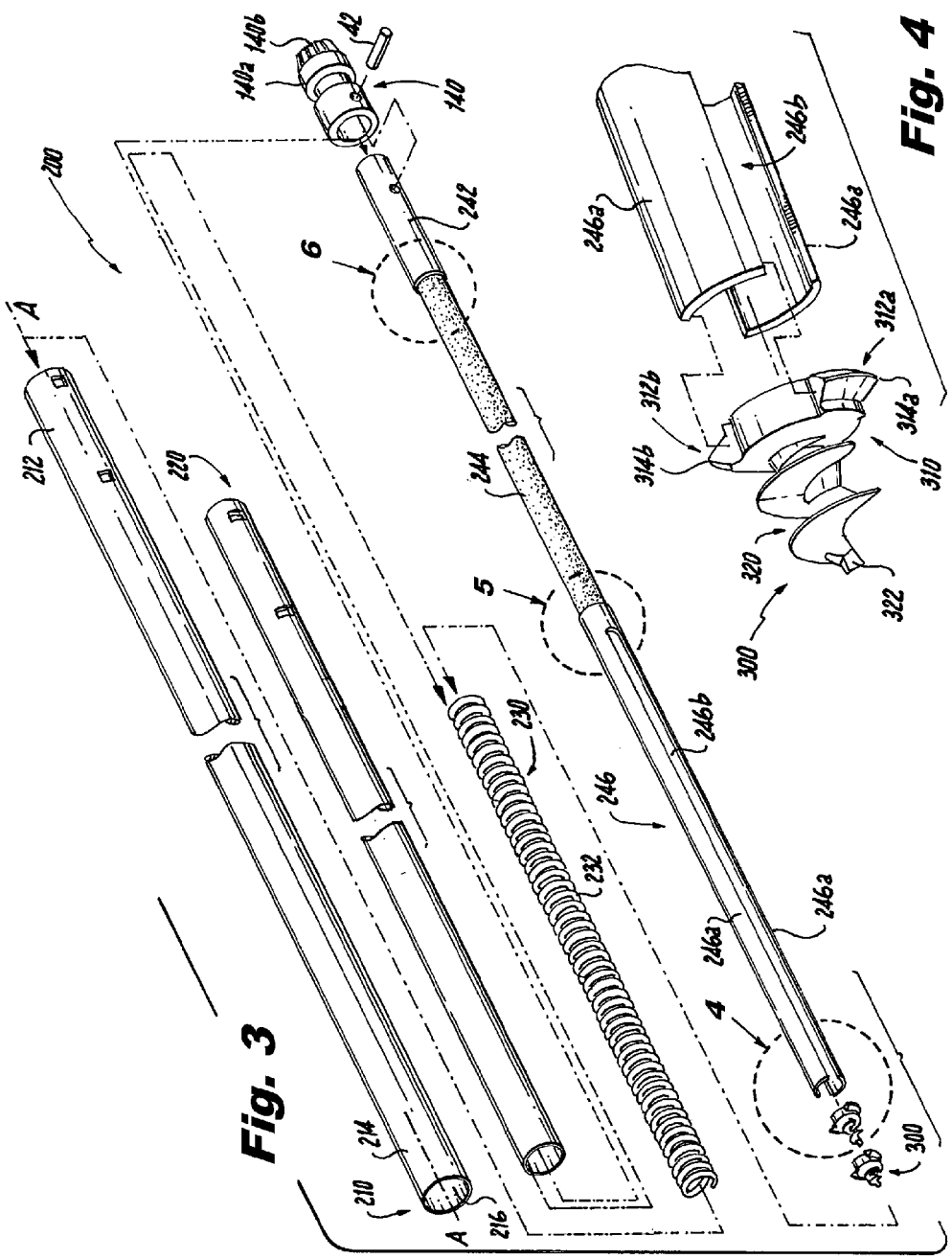

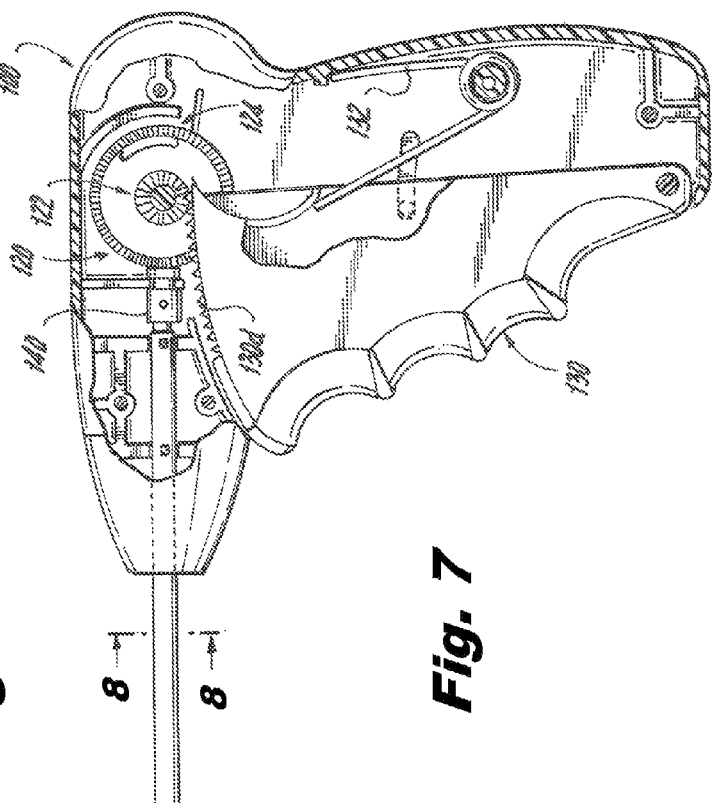
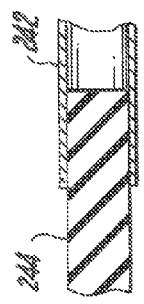
Fig. 6
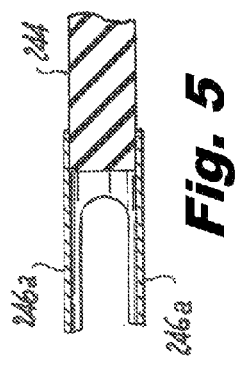
Fig. 5
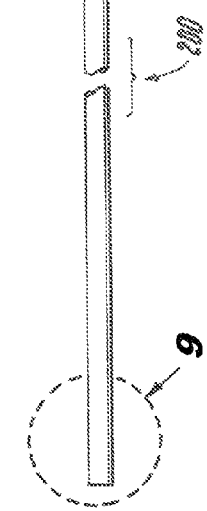
Fig. 7
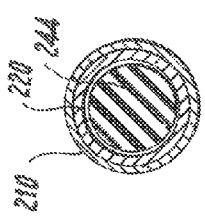
Fig. 8

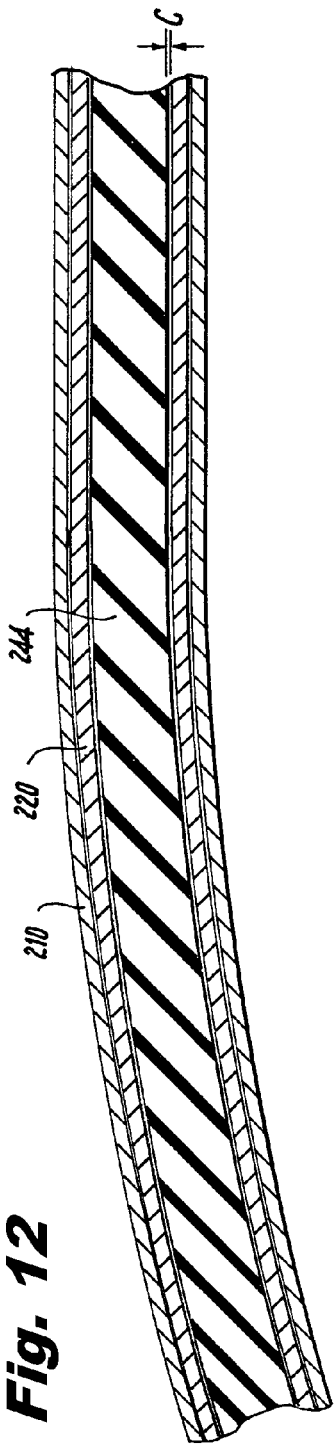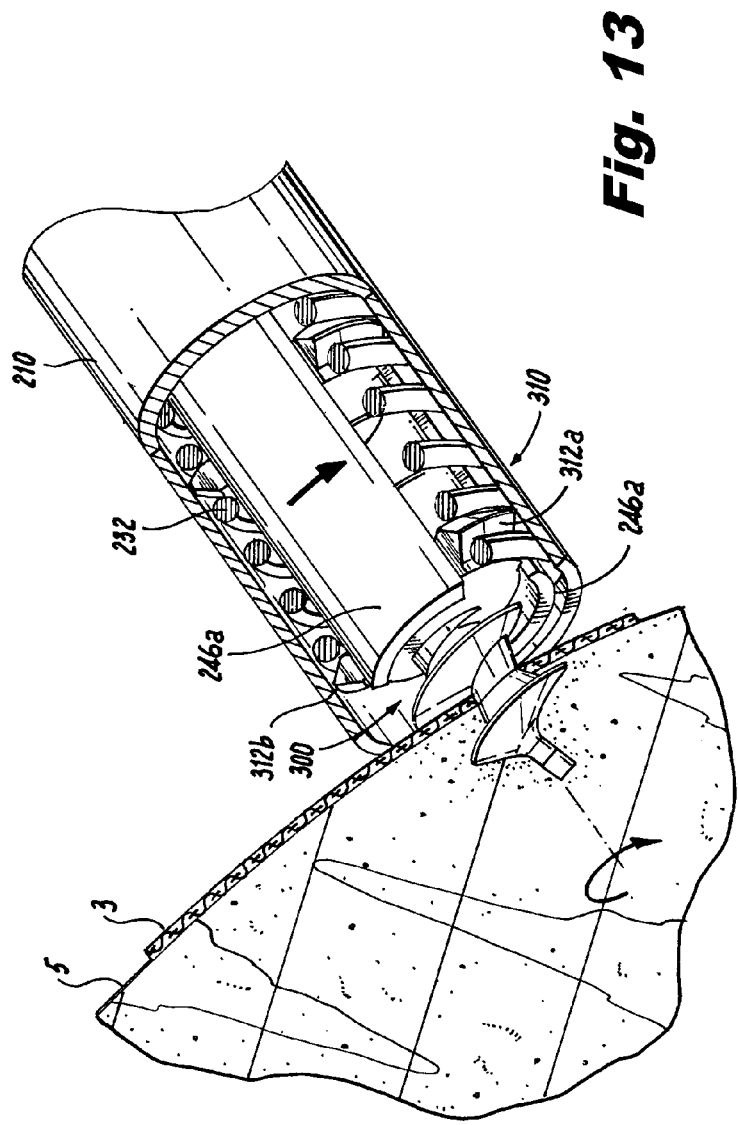

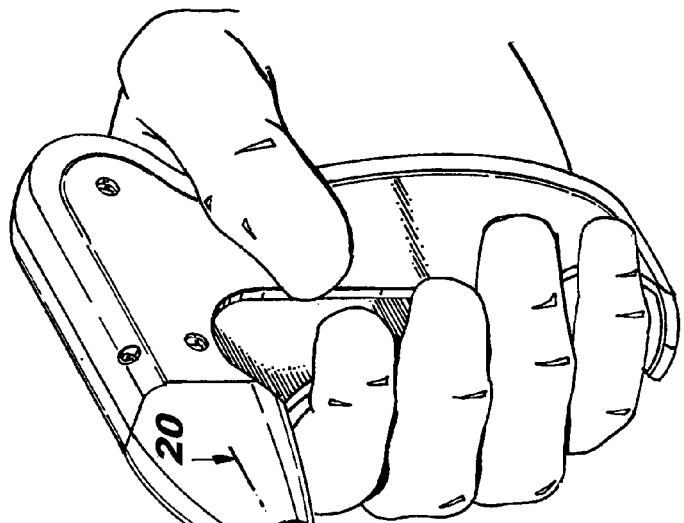
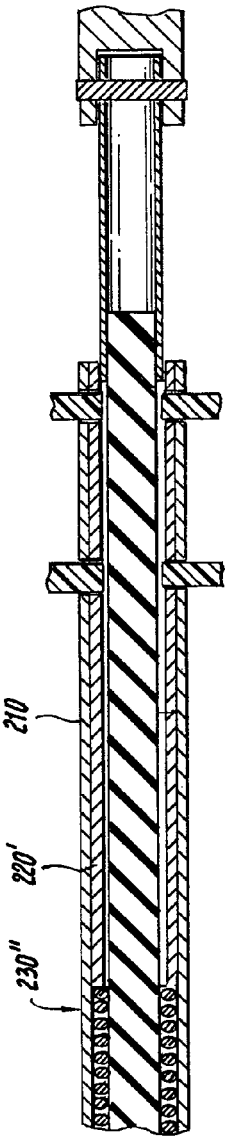
Fig. 19
Fig. 20

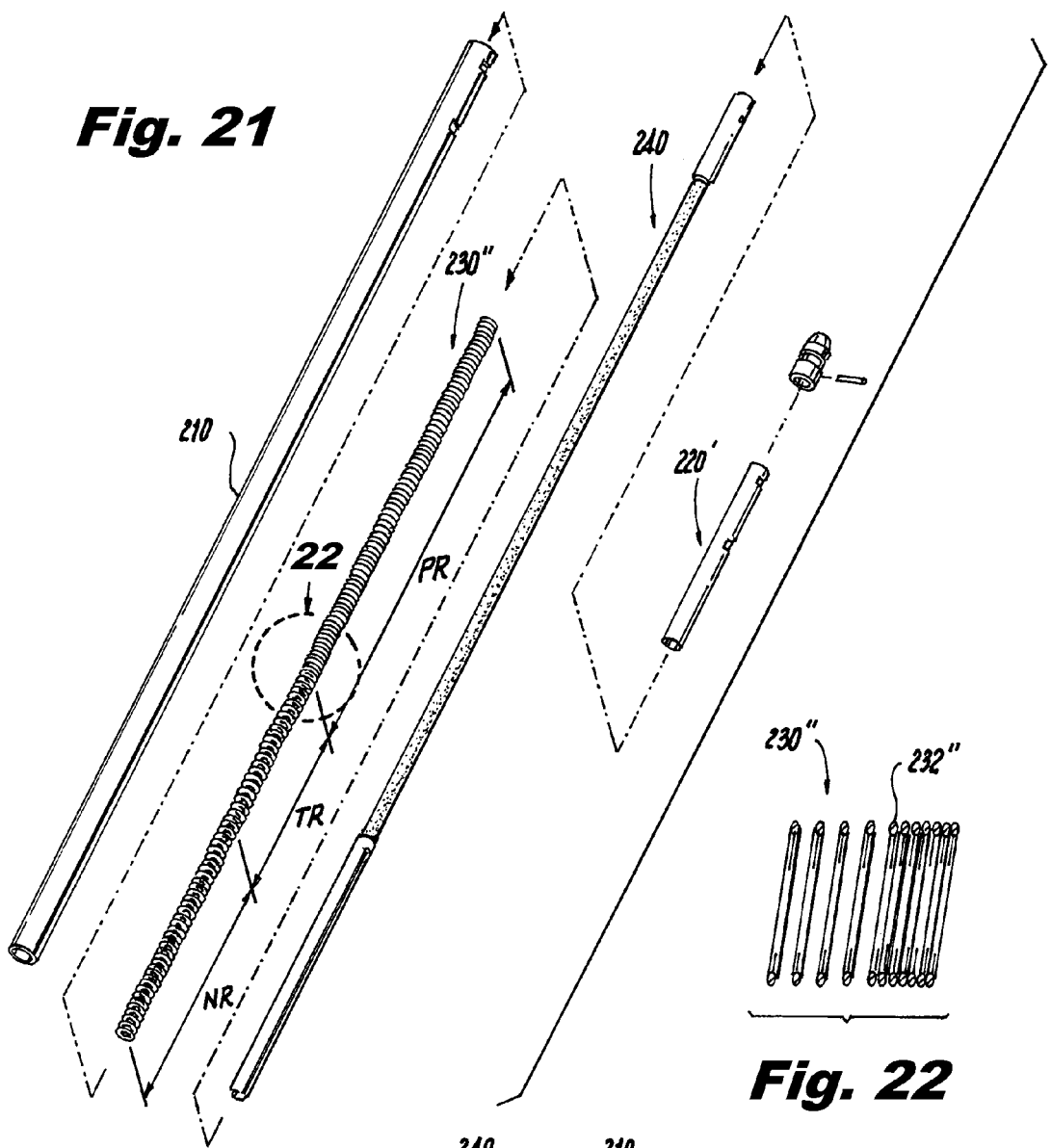
Fig. 21
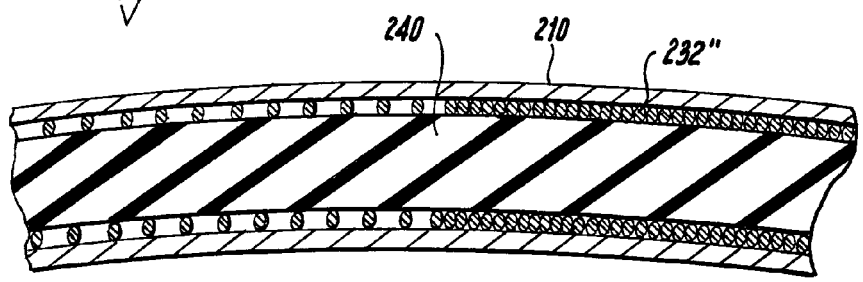
Fig. 22
Fig. 23

FLEX CABLE AND SPRING-LOADED TUBE FOR TACKING DEVICE

CROSS-REFERENCE TO RELATED APPLICATIONS

This application claims the benefit of and priority to U.S. Provisional Patent Application No. 61/776,811, filed Mar. 12, 2013, the entire disclosure of which is incorporated by reference herein.

BACKGROUND

1. Technical Field

The present disclosure relates generally to surgical fastener appliers, and more particularly, a surgical fastener applier configured for continued operation in the presence of a bending load applied to an endoscopic portion thereof.

2. Description of Related Art

Various surgical procedures require instruments capable of applying fasteners to tissue to form tissue connections or to secure objects to tissue. For example, during hernia repair it is often desirable to fasten a mesh to body tissue. In certain hernias, such as direct or indirect inguinal hernias, a part of the intestine protrudes through a defect in the support abdominal wall to form a hernial sac. The defect may be repaired using an open surgery procedure in which a relatively large incision is made and the hernia is closed off outside the abdominal wall by suturing. The mesh is attached with sutures over the opening to provide reinforcement.

Minimally invasive, e.g., endoscopic or laparoscopic, surgical procedures are currently available to repair a hernia. In laparoscopic procedures surgery is performed in the abdomen through a small incision while in endoscopic procedures, surgery is performed through narrow endoscopic tubes or cannulas inserted through small incisions in the body. Laparoscopic and endoscopic procedures generally utilize long and narrow instruments capable of reaching deep within the body and configured to seal with the incision or tube they are inserted through. Additionally, the instruments must be capable of being actuated remotely, that is, from outside the body.

Currently, minimally invasive surgical techniques for hernia repair utilize surgical fasteners, e.g., surgical tacks, staples, and clips, to secure the mesh to the tissue to provide reinforcement to the repair and structure for encouraging tissue ingrowth. Surgical fasteners are often applied through an elongate instrument for delivery to the mesh, and are manipulated from outside a body cavity. Challenges are presented in the course of minimally invasive surgical procedures when an elongate instrument is flexed or deflected, e.g., when being manipulated by an operator, encountering an obstruction, or otherwise subject to a bending load. Accordingly, there is a need for an improved instrument configured to withstand a bending load for delivering surgical fasteners to a minimally invasive surgical procedure site.

SUMMARY

A surgical fastener applier is disclosed and includes a handle portion, a tubular member extending from the handle portion and defining a longitudinal axis, a drive member rotatably supported in the tubular member and in the handle portion, and a plurality of fasteners. The drive member is configured to rotate while in a deflected condition with respect to the longitudinal axis. The plurality of fasteners is disposed within the tubular member and is configured to engage a portion of the drive member such that rotational motion of the drive member causes distal advancement of at least one fastener of the plurality of fasteners through the tubular member.

According to one embodiment of the present disclosure, the drive member includes a proximal portion, a central portion, and a distal portion, the central portion having a flexible configuration. According to another embodiment, a distal portion of the drive member defines at least one time to engage a portion of at least one fastener of the plurality of fasteners. In yet another embodiment, the drive member is configured for deflection relative to the longitudinal axis at a rate different than that of the tubular member.

In one embodiment of the present disclosure, the surgical fastener applier further includes a drive gear operatively connecting the handle portion and the drive member. The drive gear may be configured to transmit rotational motion to the drive member upon actuation of the handle portion. In another embodiment the drive member includes a proximal portion, a central portion, and a distal portion, the central portion having a torsionally stiff configuration. In yet another embodiment, the drive member includes a proximal portion, a central portion, and a distal portion, the central portion configured for continued rotation in the presence of a bending load.

In another embodiment of the present disclosure, the tubular member includes a coiled spring circumferentially disposed about a portion of the drive member. In one embodiment of the present disclosure, the coiled spring is configured to engage a portion of at least one of the plurality of fasteners.

According to another embodiment of the present disclosure, a surgical fastener applier is disclosed, and includes a handle portion, a tubular member, a stiffener member, a coiled spring, a drive member, and a plurality of fasteners. The tubular member extends from the handle portion and defines a longitudinal axis. The stiffener member has a different rigidity than the tubular member. The coiled spring is disposed within the tubular member and is configured to maintain a substantially straight condition of the tubular member. The drive member is rotatably supported in the tubular member and in the handle portion, and includes a portion having a longitudinally flexible and torsionally stiff configuration. The plurality of fasteners is disposed within the tubular member and each fastener is configured to engage a portion of the drive member such that rotational motion of the drive member causes distal advancement of at least one fastener of the plurality of fasteners through the tubular member. At least one fastener of the plurality of fasteners is engaged with the coiled spring. A clearance is defined between the drive member and the tubular member, and the drive member is configured for rotation in a deflected condition.

According to one embodiment, the coiled spring has a substantially constant pitch along the longitudinal axis. The coiled spring may have a variable pitch along the longitudinal axis. According to another embodiment, the coiled spring includes an axially compressed portion. The axially compressed portion of the coiled spring may be maintained via a welding to an inner surface of the tubular member. The axially compressed portion of the coiled spring may be configured to undergo deflection with respect to the longitudinal axis at different rate than the remainder of the coiled spring. According to yet another embodiment, the axially compressed portion of the coiled spring is located at a proximal portion of the coiled spring.

BRIEF DESCRIPTION OF THE DRAWINGS

Embodiments of the present disclosure will be appreciated by reference to the drawings, wherein:

FIG. 2 is a perspective view, with parts-separated, of the surgical fastener applier of FIG. 1;

FIG. 2a is an enlarged view of a pinion gear as highlighted in the area of detail identified in FIG. 2;

FIG. 3 is a perspective view, with parts-separated, of a drive portion of the surgical fastener applier of FIG. 1;

FIG. 4 is an enlarged view of the area of detail identified in FIG. 3;

FIG. 5 is a longitudinal cross-sectional view taken along the area of detail identified in FIG. 3;

FIG. 6 is a longitudinal cross-sectional view taken along the area of detail identified in FIG. 3;

FIG. 7 is a side elevational view, partially cut-away, of the surgical fastener applier of FIG. 1;

FIG. 8 is a transverse cross-sectional view taken along section line 8-8 of FIG. 7;

FIG. 12 is a cross-sectional view taken along section line 12-12 of FIG. 11;

FIG. 13 is a cut-away view of the area of detail identified in FIG. 11;

FIG. 19 is a perspective view of an alternative embodiment of a surgical fastener applier according to the present disclosure;

FIG. 20 is a cross-sectional view taken along section line 20-20 of FIG. 19;

FIG. 21 is a perspective view, with parts-separated, of the surgical fastener applier shown in FIG. 19;

FIG. 22 is an enlarged cross-sectional view of the area of detail identified in FIG. 21; and FIG. 23 is a cross-sectional view taken along section line 23-23 of FIG. 19.

DETAILED DESCRIPTION OF THE EMBODIMENTS

With reference now to the drawings wherein like numerals represent like elements throughout the several views, the presently-disclosed surgical fastener applier will be described. As used herein, the term "operator" may refer to any user, e.g., a nurse, doctor, or clinician, of the presently-disclosed surgical fastener applier. Further, the term "distal" refers to that portion of the applier, or component thereof, further from the operator while the term "proximal" refers to that portion of the surgical fastener applier, or component thereof, closer to the operator.

Figure 1:
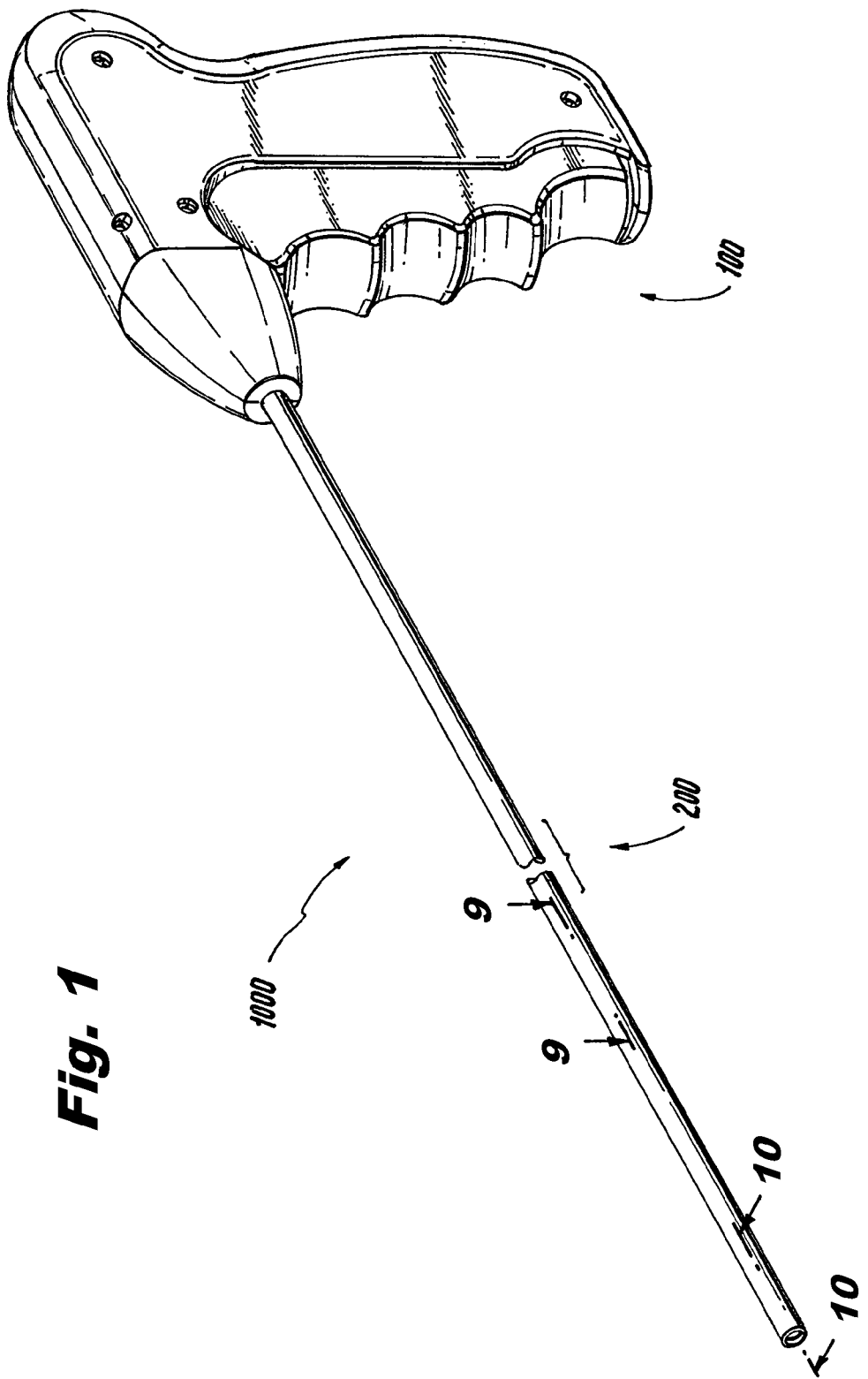
FIG. 1 is a perspective view of a surgical fastener applier according to the present disclosure.

Referring initially to FIG. 1, a surgical fastener applier 1000 is shown. Surgical fastener applier 1000 includes a handle portion or assembly 100 and a drive portion or assembly 200 extending away from the handle portion 100. Handle portion 100, as shown, may have a manual, pistol-type ergonomic grip configuration suitable for grasping by an operator. Drive portion 200, as shown, has an elongate tubular configuration and is sized for endoscopic insertion into a body cavity.

Turning to FIG. 2, handle portion 100 of surgical fastener applier 1000 includes a pair of housing half-sections 110a, 110b, a drive gear 120, and a trigger 130. Handle portion 100 is connected to the drive portion 200 of the surgical fastener applier 1000 via a collar 140, as will be described further below.

Housing half-sections 110a, 110b define an interior chamber such that, upon assembly, drive gear 120 is disposed within housing half-sections 110a, 110b. Drive gear 120 includes a pinion gear 122 and a bevel gear 124. Drive gear 120 operates in coordination with trigger 130 and a trigger spring 132, as will be described further below.

Referring additionally to FIG. 2a, pinion gear 122 includes a hub 122a having a circular configuration and defining a series of radially outward ridges or teeth 122b. An arm 122c extends radially away from the hub 122a. Arm 122c has a flat, tapered configuration, and tangentially intersects a flat side of the hub 122a. Arm 122c includes a cam 122d having a sloped configuration and protruding from a major surface of the arm 122c and away from the hub 122a.

Bevel gear 124 has a circular, disc-shaped configuration and defines a series of circumferentially-disposed ridges or teeth 124a extending from a major surface thereof. Bevel gear 124 also includes an arcuate slot 124b formed radially inward on the major surface of the bevel gear 124 with respect to the teeth 122b of pinion gear 122, and is configured to receive cam 122d of the pinion gear 122, as will be described further below.

Trigger 130, as shown, includes a body 130a which defines an engagement surface 130b configured for manual engagement by, e.g., the fingers of an operator. With additional reference to FIG. 7, trigger 130 includes an arcuate proximal surface 130c including a series of teeth 130d. Teeth 130d of trigger 130 are configured to interengage teeth 122b of pinion gear 122, as will be described further below. Trigger spring 132, as shown, may be configured as a torsional spring, and is operably coupled with the trigger 130, as will be described further below.

Turning now to FIG. 3, the components of the drive portion 200 will be described in detail. Drive portion 200 includes an outer tubular member 210, a stiffener member 220, a coiled spring 230 and a drive member 240. Drive portion 200 is configured and dimensioned to accommodate a series of surgical fasteners 300, as will be described further below.

Outer tubular member 210 of drive portion 200 is an elongate, tubular member defining a longitudinal axis "A" and having a proximal portion 212 and a distal portion 214, and defining an interior channel or lumen 216 within which other portions of the drive portion 200 are disposed, as will be described further below. Tubular member 210 may be formed of any suitable biocompatible material, e.g., stainless steel.

Stiffener member 220 is an elongate tubular member dimensioned to fit within the interior lumen 216 of and along the proximal portion 212 of outer tubular member 210. Stiffener member 220 is formed of a material having a different, e.g., higher, rigidity than the coiled spring 230, as will be described further below. Coiled spring 230 also has a different rigidity than the outer tubular member 210. Spring 230 may be made of a stainless steel, such as type 302 stainless steel.

Figure 9:
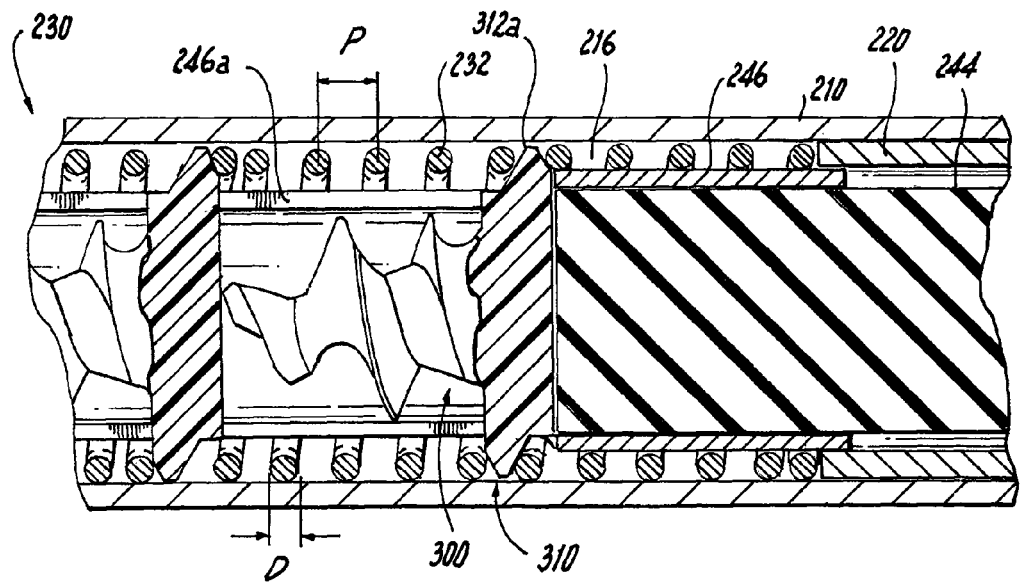
FIG. 9 is a longitudinal cross-sectional view taken along section line 9-9 of FIG. 1.

Coiled spring 230 is configured as a tubular spring, i.e., coiled spring 230 is wound in a manner such that the body 232 of coiled spring 230 has a diameter "D" and defines a pitch "P" (FIG. 9). Accordingly, the spacing between successive winds or coils of the body 232 of the coiled spring 230 define a substantially spiraled path within which a surgical fastener 300 is configured to rotate and travel, as will be described further below. Owing to the resilient, i.e., elastic, configuration of coiled spring 230, coiled spring 230 has a different rigidity than stiffener member 200 described above, i.e., coiled spring 230 is more flexible than stiffener member 220. Accordingly, stiffener member 220 may be formed of a material with a relatively higher rigidity than coiled spring 230. Stiffener member 220 may be formed of, e.g., a polymeric or metallic material.

Drive member 240 includes a proximal portion 242, a central portion 244, and a distal driving portion 246. Drive member 240 has a generally tubular configuration, and is dimensioned to extend within stiffener member 220 and coiled spring 230, and within the interior channel 216 of the outer tubular member 210. Drive member 240 may have any suitable longitudinally flexible, torsionally stiff configuration, e.g., a flexible cable. It is contemplated that each of proximal portion 242 and distal driving portion 246 of drive member 240 have a relatively more rigid or stiff configuration as compared to central portion 244 of drive member 240, i.e., central portion 244 of drive member 240 defines a relatively more flexible region of drive member 240 as compared to proximal portion 242 and distal driving portion 246 of drive member 240. In this manner, central portion 244 of drive member 240 has different mechanical properties relative to the remainder of drive member 240. For example, the central portion may be formed of a multi-strand twisted cable, a braided cable or a tube. The tube may be laser cut in patterns to increase flexibility.

Proximal portion 242 of the drive member 240 is configured to be fit within a collar 140, as shown. Collar 140 includes a tubular body 140a having a proximal beveled portion 140b. Drive member 240 is attached to handle portion 100 (FIG. 1) via collar 140, and may be secured with fasteners 142, which may be, e.g., pins, screws, or bolts. Alternatively, the proximal portion 242 of drive member 240 may be integrally formed, e.g., welded, brazed, or adhered with collar 140. In some embodiments, drive member 240 may be press-fit into collar 140.

Central portion 244 of drive member 240 is a substantially cylindrical portion that torsionally stiff, yet capable of bending along the longitudinal axis A, i.e., central portion 244 of drive member 240 is configured to bend along the longitudinal axis A while maintaining a substantially constant radial configuration. It is contemplated that central portion 244 of drive member 240 continues to rotate, in the presence of external forces. Accordingly, central portion 244 may be formed of a flexible, yet high-strength material, e.g., stainless steel configured as previously described.

Distal driving portion 246 of drive member 240 has a forked or splined configuration, i.e., distal driving portion 246 defines a pair of tines 246a circumferentially spaced by a pair of respective radial gaps 246b. Tines 246a are configured to engage a portion of surgical fasteners 300 to transmit rotational forces to surgical fasteners 300, as will be described further below.

Referring additionally to FIG. 4, surgical fasteners 300 will now be described in detail. Surgical fasteners 300, as shown, are configured to be disposed within the interior channel 216 of outer tubular member 210. Surgical fasteners 300 may be loaded into outer tubular member 210 in an axially stacked column. Each surgical fastener 300 includes a head section 310, a mesh retention section 320, and a tissue-snaring section 322. Head section 310 includes a pair of opposing threaded sections 312a, 312b having respective radially outer head threads 314a, 314b, and a pair of opposing open or slotted sections 316a, 316b. Slotted sections 316a, 316b are configured to receive a respective time 246a of the distal driving portion 246 of drive member 240 (FIG. 3), as will be described further below. Mesh retention section 320 of surgical fastener 300 functions to lock, anchor, or otherwise retain a surgical mesh "M" (FIG. 11) onto surgical fastener 300 when surgical fastener 300 is advanced into mesh M, as will be described further below. An exemplary surgical fastener is disclosed in U.S. Patent Application Publication No. 2011/0282401 to Corradi, et al., the entire contents of which are incorporated by reference herein.

Turning now to FIGS. 5-10, surgical fastener applier 1000 is shown with the above-described components assembled. Housing half-sections 110a, 110b of handle portion 100 are coupled in any conventional manner, e.g., snap-fit or ultrasonic welding. Outer tubular member 210 may be e.g., clamped or welded with handle portion 100. Collar 140 is rotatably disposed within a distal portion of the handle portion 100. Collar 140 may be held in place by a portion of housing half-sections 110a, 110b, may be provided with a friction-reducing wheel or bearing, or other rotatable coupling as is known in the art.

With additional reference to FIG. 3, the assembled housing half-sections 110a, 110b define an interior chamber within which drive gear 120 is disposed. Pinion gear 122 and bevel gear 124 are rotatably mounted, e.g., supported by a pin, axle, or dowel (not shown) within the housing half-sections 110a, 110b such that pinion gear 122 and bevel gear 124 are laterally adjacent and disposed in concentric relation. In this manner, drive gear 120 is arranged such that the cam 122d protruding from the arm 122c of the pinion gear is aligned to enter the arcuate slot 124b of bevel gear 124 to rotate the bevel gear 124.

The proximal beveled end 140b of the collar 140 is disposed such that the teeth 124c of the bevel gear 124 are held in interengaging relation with the proximal beveled end 140b of the collar 140. Trigger 130 is mounted distally below the drive gear 120 such that the teeth 130d on the proximal surface 130c of trigger 130 are disposed to interengage the teeth 122b of pinion gear 122. Trigger spring 132 is disposed within the handle portion 100 proximally of the trigger 130 to bias the trigger 130 in a distal direction and to provide a counterforce to manual squeezing of the trigger 130. Trigger spring 132 may be configured to provide a predetermined resistance to compression, e.g., to increase tactile feedback to an operator or to minimize slipping of the manual engagement of handle portion 100 by an operator.

As described above, the drive portion 200 extends distally away from the handle portion 100. The outer tubular member 210 of the drive portion is mounted in a rotationally fixed manner with respect to the handle portion 100. The stiffener member 220 is concentrically disposed within the outer tubular member 210 along a proximal portion 212 of the outer tubular member 210. Stiffener member 220 is rotationally fixed with respect to the outer tubular member 210, and may be secured to an inner surface of the outer tubular member 210 in any conventional manner, e.g., adhesion, welding, or press-fit.

Coiled spring 230, as shown, is concentrically disposed within the outer tubular member 210 along a distal portion 214 of the outer tubular member 210. Coiled spring 230 is also rotationally fixed with respect to the outer tubular member 210 and may be secured to an inner surface of the outer tubular member in any conventional manner, e.g., adhesion, welding, brazing, or press-fit. Stiffener member 220 and coiled spring 230 may be disposed in a longitudinally adjacent, e.g., axially abutting relation within the interior channel 216 of outer tubular member 210, or a gap may be defined between adjoining ends of the stiffener member 220 and coiled spring 230.

Drive member 240, as shown, is concentrically disposed within both the stiffener member 220 and coiled spring 230, and extends substantially the length of the outer tubular member 210. The proximal portion 242 of drive member 240 is secured within the distal portion 144 of collar 140 via pins 142. In this manner, drive member 240 is free to rotate within respect to the outer tubular member 210.

Figure 10:
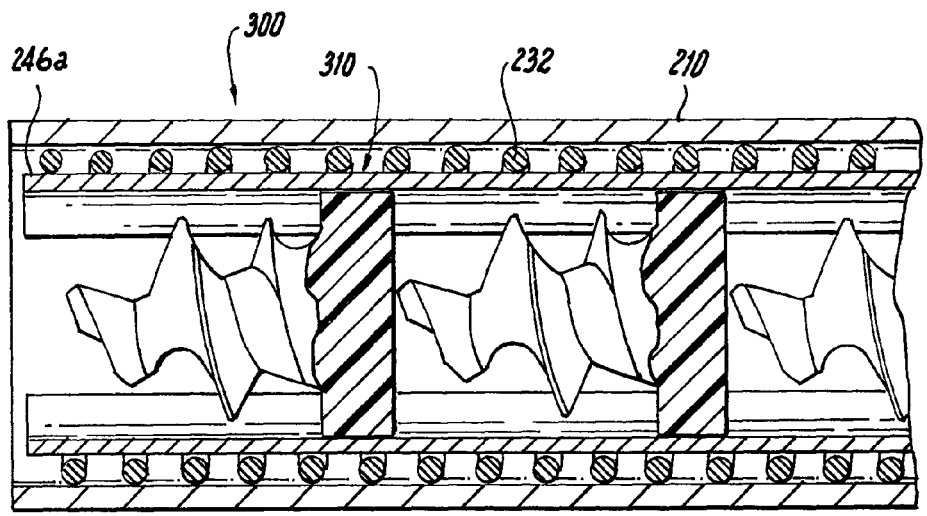
FIG. 10 is a cross-sectional view taken along section line 10-10 of FIG. 1.

Turning momentarily to FIGS. 9 and 10, the surgical fasteners 300 are disposed within the coiled spring 230 such that the tines 246a of the distal driving portion 240 extend axially through the slotted sections 316a, 316b of the head section 310. Accordingly, the opposing thread sections 312a, 312b of the surgical fasteners 300 are disposed between the radial gaps 246b (FIG. 3) defined by the tines 246a such that, upon rotation of the drive member 240, the tines 246b are disposed to exert a torque on the head section 310 of the surgical fasteners 300. As described above, the opposing thread sections 312a, 312b of surgical fasteners 300 are disposed within the helical path defined by the spaces between successive winds or coils of the coiled spring 230. As will be described further below, the inter-engagement of the head section 310 of the surgical fasteners 300, in particular, the opposing thread sections 312a, 312b and the coiled spring 230 provides a guided, helical path along which the surgical fasteners 300 advance upon rotation.

Figure 11:
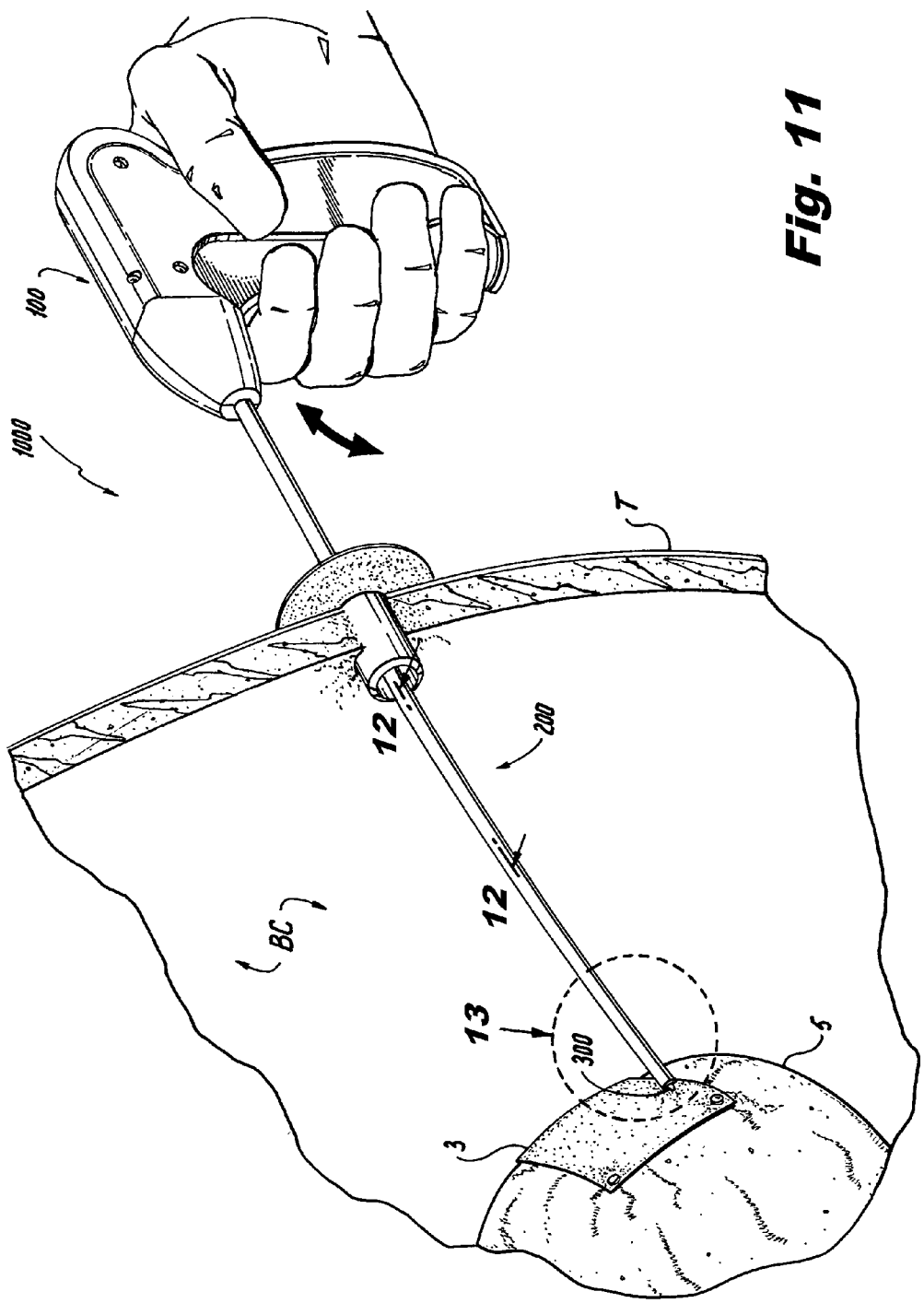
FIG. 11 is a perspective view of the surgical fastener applier shown inserted through a body wall, shown in cut-away.
Figures 14, 15:
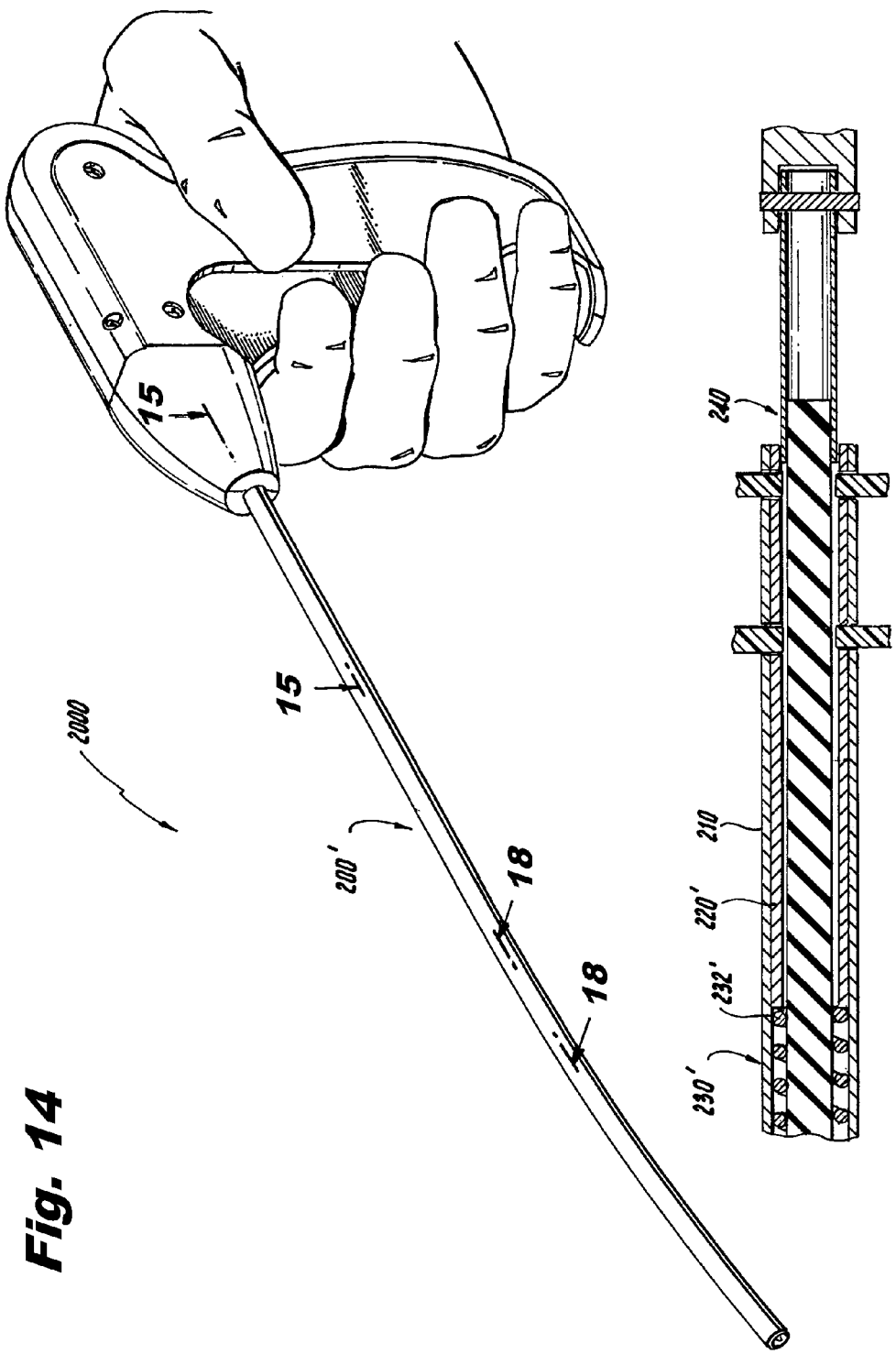
FIG. 14 is a perspective view of an alternative embodiment of a surgical fastener applier according to the present disclosure.
FIG. 15 is a cross-sectional view taken along section line 15-15 of FIG. 14.
Figure 16:
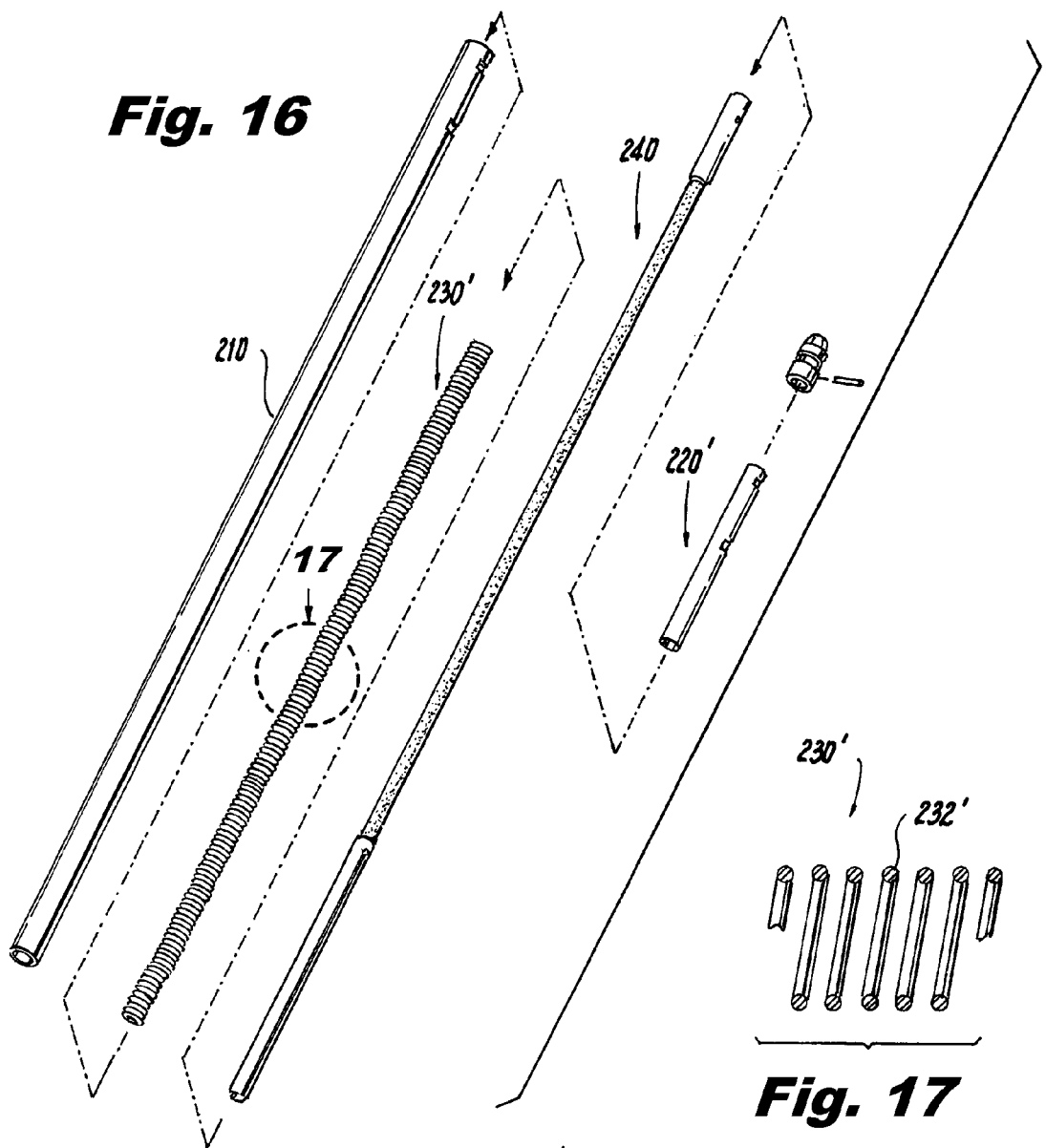
FIG. 16 is a perspective view, with parts-separated, of the surgical fastener applier shown in FIG. 14.
Figure 17:
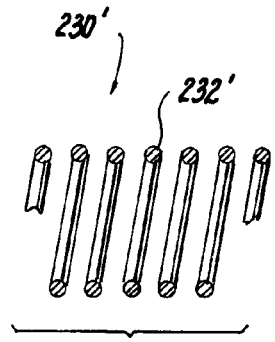
FIG. 17 is an enlarged cross-sectional view of the area of detail identified in FIG. 16.
Figure 18:
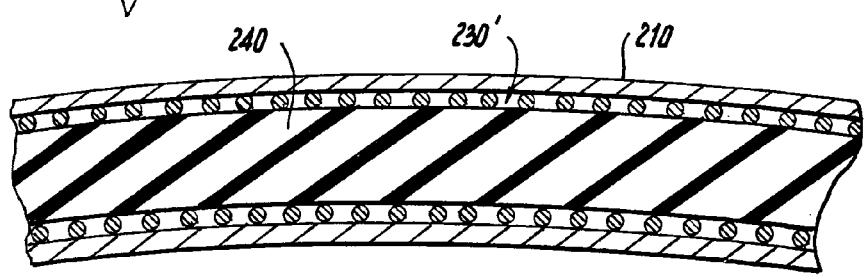
FIG. 18 is a cross-sectional view taken along section line 18-18 of FIG. 14.

With additional reference now to FIG. 11, the operation of the surgical fastener applier 1000 will be described in detail. Surgical fastener applier 1000 may be inserted through an opening, e.g., an incision or naturally-occurring orifice, in a layer of tissue "T" and into a body cavity "BC" below. Surgical fastener applier 1000 may be inserted through a surgical access port, as shown, to minimize trauma to the surrounding layer of tissue "T." Upon actuation of the trigger 130, i.e., the concentric movement of trigger 130 with respect to housing half-sections 110a, 110b, the series of teeth 130d on the proximal portion of the trigger 130 interengages the radially outward teeth 122b of the pinion gear 122 to cause rotation of the pinion gear 122 within the interior chamber of defined by the handle portion 100. As the arm 122c of the pinion gear 122 travels in a circular path with the rotation of the hub 122a of pinion gear 122, the cam 122d extending from the arm 122c is brought into alignment with and enters the arcuate slot 124b of the bevel gear 124, causing rotation of the bevel gear 124. Due to the sloped configuration of the cam 122d, the cam 122d is configured to drive the bevel gear 24 in a first, forward rotational direction, and is configured to disengage, i.e., slip, from the arcuate slot 124b of the bevel gear 122d in a second, reverse rotational direction. Such a configuration provides an anti-reverse drive for the drive gear 120, and is described in detail in U.S. Pat. No. 8,114,099 to Shipp, the entire contents of which is incorporated by reference herein.

As the bevel gear 124 rotates within the interior chamber defined by the handle portion 100, the teeth 124a of the bevel gear 124 interengage the proximal beveled portion of collar 140. As the collar 140 is secured to the drive member 240 via pins 142, actuation of the handle portion 100 of the surgical fastener apparatus 1000 in the manner described above causes rotation of the drive member 240. As the drive member 240 rotates with the collar 140, the tines 246a of the distal driving portion 246 of the drive member 240 cause rotation of the surgical fasteners 300. As the head portion 310, specifically, opposing thread sections 312a, 312b of each surgical fastener 300 are engaged within the helical path defined by the spacing of successive winds or coils of coiled spring 230, rotation of each surgical fastener 300 causes distal advancement of each surgical fastener through the drive portion 200 of surgical fastener applier 1000. As shown, surgical fastener applier 1000 may be placed above an internal body structure "S," e.g., an abdominal wall, and brought into close proximity with a mesh "M" such that surgical fastener applier 1000 is positioned to advance one or more surgical fasteners 300 through mesh "M" and into the internal structure "S."

As shown, surgical fastener applier 1000 may be subject to a bending load, i.e., surgical fastener applier 1000 may bow, flex, or otherwise deflect in response to manipulation of surgical fastener 1000 by an operator during the course of a minimally invasive procedure.

Turning now to FIGS. 12 and 13, the central portion 244 of drive member 240 is shown disposed within the interior channel 212 of the drive portion 200 of surgical fastener applier 1000 such that a clearance "C" is defined between the outer surface of the drive member 240 and the interior surface of the stiffener member 220 or coiled spring 230. Clearance "C" affords the drive member 240 a degree of movement within the drive portion 100 of surgical fastener applier 1000 under a bending load. Owing to the flexible, yet torsionally stiff configuration of the central portion 244 of drive member 240, central portion 244 of drive member 240 facilitates continued freedom of rotation of the drive member 240 under deflection. Thus, the central portion 244 of drive member 240 deflects under a bending load at a rate different than outer tubular member 210. In this manner, surgical fastener applier 1000 is configured to operate to apply surgical fasteners 300 under a bending load that would have bound a surgical fastener applier devoid of a drive member having some flexible portion thereof.

Turning to FIGS. 14-18, an alternative configuration of a surgical fastener applier, generally designated 2000, will be described. Surgical fastener applier 2000 is substantially similar to surgical fastener 1000 above, and will only be described to discuss the differences therein. Surgical fastener applier 2000 includes a drive portion 200' that includes outer tubular member 210, a stiffener member 220', a coiled spring 230', and drive member 240.

Stiffener member 220' is an elongate tubular member dimensioned to fit within the interior channel 216 along the proximal portion 212 of outer tubular member 210. Stiffener member 220' has a different axial length, i.e., stiffener member 220' is axially shorter than stiffener member 220 described above. In accordance with the present disclosure and the present embodiment, it is contemplated that stiffener member 220' has an axial length of about 1.5 inches. Stiffener member 220' is formed of a material having a different, e.g., higher, rigidity than the coiled spring 230', as will be described further below. Accordingly, stiffener member 220' may be formed of a high-strength polymeric or metallic material, e.g., stainless steel.

Coiled spring 230' is configured as a tubular spring, i.e., coiled spring 230' is wound in a manner such that the body 232' of coiled spring 230' defines a pitch. Coiled spring 230' is disposed longitudinally adjacent the stiffener member 220' within the outer tubular member 210. Owing to the axially shortened configuration of stiffener member 220' described above, coiled spring 230' has a different axial length, i.e., coiled spring 230' is axially longer than coiled spring 230 described above. Coiled spring 230' defines a substantially spiraled path within which a surgical fastener 300 is configured to rotate in the manner described above with respect to surgical fastener applier 1000. Owing to the resilient, i.e., elastic, configuration of coiled spring 230', coiled spring 230' has a different rigidity than stiffener member 220' described above, i.e., coiled spring 230' is more flexible than stiffener member 220'.

During use, surgical fastener applier 2000 may be subject to bending loads in the same manner as surgical fastener applier 1000 described above. Owing to the different axial lengths of stiffener member 220' and coiled spring 230', the flexibility afforded to the drive portion 200' by the configuration of the coiled spring 230' is present along an axially longer section of drive portion 200' as opposed to drive portion 200. Correspondingly, drive portion 200' includes an axially shorter region of increased flexibility afforded by the stiffener member 220' as compared to the drive portion 200. Such a flexibility profile may be desirable, e.g., in anticipation of increased bending loads or a bending profile including stress concentrations along locations of drive portion 200' of surgical fastener applier 2000 proximally located with respect to corresponding locations of drive portion 200 of surgical fastener applier 1000.

Turning to FIGS. 19-23, an alternative configuration of a surgical fastener applier, generally designated 3000, will be described. Surgical fastener applier 3000 is substantially similar to surgical fastener 1000 and surgical fastener 2000 described above, and will only be described to discuss the differences therein. Surgical fastener applier 3000 includes a drive portion 200" and includes outer tubular member 210, stiffener member 220', a coiled spring 230", and drive member 240.

Coiled spring 230" is configured as a tubular spring, i.e., coiled spring 230' is wound in a manner such that the body 232" of coiled spring 230" defines a variable pitch along its axial length. Coiled spring 230" may be maintained in an axially compressed position, e.g., by welding successive coils to each other and/or to the inner surface of outer tube 210, or by plastic deformation of portions of coiled spring 230" along proximal portions of the coiled spring 230, i.e., coiled spring 230" defines a smaller pitch along proximal portions of coiled spring 230" and a gradually larger pitch along distal portions of coiled spring 230". Accordingly, coiled spring 230" may define a proximal compressed region "PR", an intermediate transition region "TR" and a distal non-compressed region "NR."

During use, surgical fastener applier 3000 may be subject to bending loads in the same manner as surgical fastener appliers 1000 and 2000 described above. Owing to the variable pitch of the coiled spring 230", the drive portion 200" of the surgical fastener 3000 may define a variable bending profile along the section of the drive portion 200" within which the coiled spring 230" is disposed. In particular, the proximal compressed region "PR" of coiled spring 230" may deflect at a different rate than the intermediate transition region "TR" and distal non-compressed region "NR" of coiled spring 230". Such a flexibility profile may be desirable, e.g., in anticipation of variable or increased bending loads or a bending profile including increased stress concentrations in the proximal direction of drive portion 200" as compared to drive portion 200.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

The invention claimed is:

1. A surgical fastener applier, comprising:
a handle portion;
a tubular member extending from the handle portion and defining a longitudinal axis;
a drive member rotatably supported in the tubular member and in the handle portion, the drive member being configured to rotate while in a deflected condition with respect to the longitudinal axis, the drive member includes a proximal portion, a central portion, and a distal portion, the distal portion of the drive member having a fork configuration including a pair of spaced apart tines defining a radial gap therebetween, the central portion being relatively more flexible as compared to at least one of the proximal portion and the distal portion; and
a plurality of fasteners disposed within the tubular member, wherein each fastener includes a threaded body portion and a head portion, the head portion defining a pair of opposed slotted sections, the pair of opposed slotted sections of each head portion receiving a respective one of the pair of tines of the distal portion of the drive member wherein rotational motion of the drive member causes distal advancement of at least one fastener of the plurality of fasteners through the tubular member.

2. The surgical fastener applier of claim 1, wherein the drive member is configured for deflection relative to the longitudinal axis at a rate different than that of the tubular member.

3. The surgical fastener applier of claim 1, further comprising a drive gear operatively connecting the handle portion and the drive member.

4. The surgical fastener applier of claim 3, wherein the drive gear is configured to transmit rotational motion to the drive member upon actuation of the handle portion.

5. The surgical fastener applier of claim 1, wherein the flexible central portion is torsionally stiff.

6. The surgical fastener applier of claim 1, wherein the flexible central portion permits continued rotation of the drive member in the presence of a bending load.

7. The surgical fastener applier of claim 1, wherein the tubular member includes a coiled spring circumferentially disposed about a portion of the drive member.

8. The surgical fastener applier of claim 7, wherein the coiled spring is configured to engage a portion of at least one of the plurality of fasteners.

9. A surgical fastener applier, comprising:
a handle portion;
a tubular member extending from the handle portion and defining a longitudinal axis;
a stiffener member having a different rigidity than the tubular member;
a coiled spring disposed within the tubular member and being configured to maintain a substantially straight condition of the tubular member;
a drive member rotatably supported in the tubular member and in the handle portion, the drive member includes a proximal portion, a central portion, and a distal portion, the distal portion of the drive member having a fork configuration defining a pair of spaced apart tines defining a radial gap therebetween, the central portion being radially flexible and torsionally stiff; and
a plurality of fasteners disposed within the tubular member, wherein each fastener includes a threaded body portion and a head portion, the head portion defining a pair of opposed slotted sections, the pair of opposed slotted sections of each head portion receiving a respective one of the pair of tines of the distal portion of the drive member wherein rotational motion of the drive member causes distal advancement of at least one fastener of the plurality of fasteners through the tubular member, at least one fastener of the plurality of fasteners engaged with the coiled spring;

wherein a clearance is defined between the drive member and the tubular member, and the drive member is configured for rotation in a deflected condition.

10. The surgical fastener applier of claim 9, wherein the coiled spring has a substantially constant pitch along the longitudinal axis.

* * * * *